United States Patent

Watabe et al.

[11] Patent Number: 5,149,426
[45] Date of Patent: Sep. 22, 1992

[54] STATIONARY PHASE FOR ENANTIOMERIC RESOLUTION IN LIQUID CHROMATOGRAPHY

[75] Inventors: Katsunori Watabe; Osamu Motokawa, both of Kyoto, Japan

[73] Assignee: Shimadzu Corporation, Kyoto, Japan

[21] Appl. No.: 734,776

[22] Filed: Jul. 23, 1991

[51] Int. Cl.$^5$ .............................................. B01D 15/08
[52] U.S. Cl. .......................... 210/198.2; 210/502.1; 210/635; 210/656; 502/401
[58] Field of Search ................... 210/635, 656, 198.2, 210/502.1; 55/386; 502/400, 401, 402

[56] References Cited

U.S. PATENT DOCUMENTS

| | | | |
|---|---|---|---|
| 4,318,819 | 3/1982 | Malloy | 210/635 |
| 4,318,820 | 3/1982 | Malloy | 210/635 |
| 4,322,310 | 3/1982 | House | 210/635 |
| 4,324,681 | 4/1982 | House | 210/635 |
| 4,604,207 | 8/1986 | Oi | 210/635 |
| 4,716,219 | 12/1987 | Eggiman | 210/635 |
| 4,830,921 | 5/1989 | Kitayama | 210/635 |
| 4,837,348 | 6/1989 | Stolowitz | 210/635 |
| 4,855,054 | 8/1989 | Williams | 210/635 |
| 4,879,038 | 11/1989 | Namikoshi | 210/635 |
| 4,919,803 | 4/1990 | Doyle | 210/635 |

FOREIGN PATENT DOCUMENTS 60-155968  1/1984  Japan ................... 210/198.2

Primary Examiner—Ernest G. Therkorn
Attorney, Agent, or Firm—Birch, Stewart, Kolasch & Birch

[57] ABSTRACT

This stationary phase for enantiomeric resolution liquid chromatography contains a chiral group of the formula:

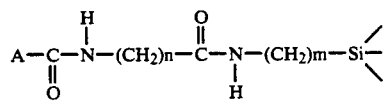

wherein A—CO— means a chiral moiety; m means an integer of not less than 3; and n means an integer of not less than 5.

This chromatographic stationary phase has a high chiral-recognition ability and, permits efficient resolution of optical isomers.

12 Claims, 3 Drawing Sheets amino acid derivative

N-acyl-amino acid amide

Chiral Moiety aminopropylsilica

STATIONARY PHASE FOR ENANTIOMERIC RESOLUTION IN LIQUID CHROMATOGRAPHY

FIELD OF INVENTION

The present invention relates to a liquid chromatographic stationary phase having a high chiralrecognition ability for fractionation and analysis of optical isomers.

BACKGROUND OF THE INVENTION

Liquid chromatography has an excellent resolution power and is applied not only to analysis but also to purification of compounds, resultantly. However, interseparation of compounds identical in general physical and chemical properties and dissimilar only in spatial configuration, such as optical isomers, requires a stationary phase having an ability to specifically discriminate optical activities.

For instance the Pirkle Column is a well-known efficient stationary phase for optical resolution of amino acids, amines, etc. that possesses a chiral center (asymmetric center) having benzoyl derivatives of phenyl glycine, which can be represented by the following typical formula

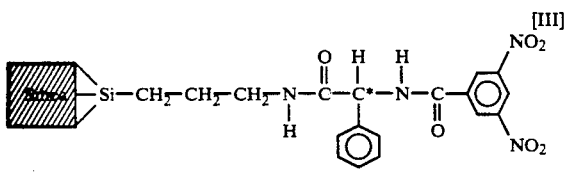

Also, Japanese Kokai Patent Application No. 60-155968 discloses a solid phase having N-carbamoyl-t-leucine as a chiral center.

However, the molecule-recognizing ability of these stationary phases for optical isomers is still insufficient and the advent of a more efficient solid phase for optical resolution liquid chromatography has been earnestly awaited.

The object of the present invention is to provide a chromatographic stationary phase which has a high molecule-recognition ability and is capable of efficient fractionation of optical isomers.

SUMMARY OF THE INVENTION

The present invention provides a stationary phase for enantiomeric resolution in chromatography which is characterized by containing a special group, having chiral-recognition as shown by the following formula:

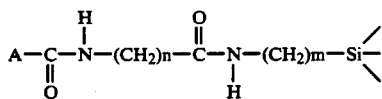

[wherein A—CO— means a chiral moiety, m is an integer of not less than 3, and n is an integer of not less than 5].

Essentially the invention is as follows. By controlling the stereo geometry of the chemically-bonded chiral phase, namely producing enough space for making the interaction between the sample molecule and the chiral moiety in the support efficient, the ability for chiral-recognition can be improved.

DETAILED DESCRIPTION OF THE INVENTION

In the stationary phase of the present invention, the chiral moiety: A—CO— may include a residue of an N-acyl amino acid, an N-carbamoyl amino acid and a N-carbamoyl-α-aromatic alkyl amine. Examples of N-acyl amino acid are N-pivaloyl-L-valine, N-3,5-dinitrobenzoyl-D-phenylglycine and the like. Examples of N-carbamoyl amino acid are N-carbamoyl -leucine, N-carbamoyl-valine and the like. Examples of N-carbamoyl-α-aromatic alkyl amine are N-carbamoyl-α-(1-naphthyl) ethyl amine and the like.

In the stationary phase of the invention, —NH—$(CH_2)_n$—CO— is interposed, as a sub-anchor moiety, between said chiral moiety and an anchor moiety (aminoalkylsilica). The symbol n represents an integer of not less than 5 and preferably 5 to 10. If n is less than 5, the separation ability of the stationary phase will not be as high as desired. While, if n is over 10, the separation ability will not be as high as desired because of increased hydrophobic interaction, unnecessary interaction for chiral recognition, between a sample molecule and a chiral stationary phase and also making easily the interaction between chiral moieties.

The symbol m represents an integer of not less than 3 and preferably 3 to 6. The aminoalkylsilica moiety linking a support to said chiral moiety may be derived from an aminoalkylsilane. The aminoalkylsilane is preferably 6-aminohexylalkoxysilane, 6-aminohexylhalogenosilane, 3-aminopropylalkoxysilane, 3-aminopropyl trihalogenosilane and the like. Suitable examples of 3-aminopropylalkoxysilane and 3-aminopropyltrihalogenosilane are 3-aminopropyl-triethoxysilane and 3-aminopropyl trichlorosilane, respectively.

The support is preferably a silica-containing support such as silica gel or the like and is desirably a finely divided powder with a uniform grain size distribution.

It is further preferable to combine a protective group with a free aminoalkyl group among groups for chiral-recognition on the surface of the support to give "a spacer". The spacer improves a chirality-recognizing ability of the stationary phase for optical isomers. Examples of the protective group are pivaloyl, trifluoroacetyl, acetyl and the like.

Research by the inventors of the present invention revealed that the conventional chromatographic stationary phases are not sufficient in interactivity between the molecule to be separated and the chiral moiety for discriminating the molecule so that the inherently high molecule-discriminating potential of the chiral moiety is not fully exploited.

Figure 2:
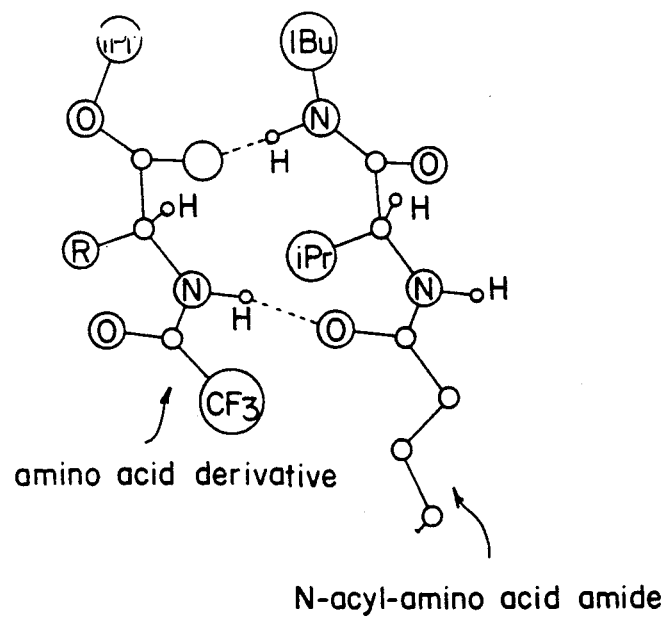
FIG. 2 is a schematic diagram showing the manner of fractionation with the prior art stationary phase.
Figure 3:
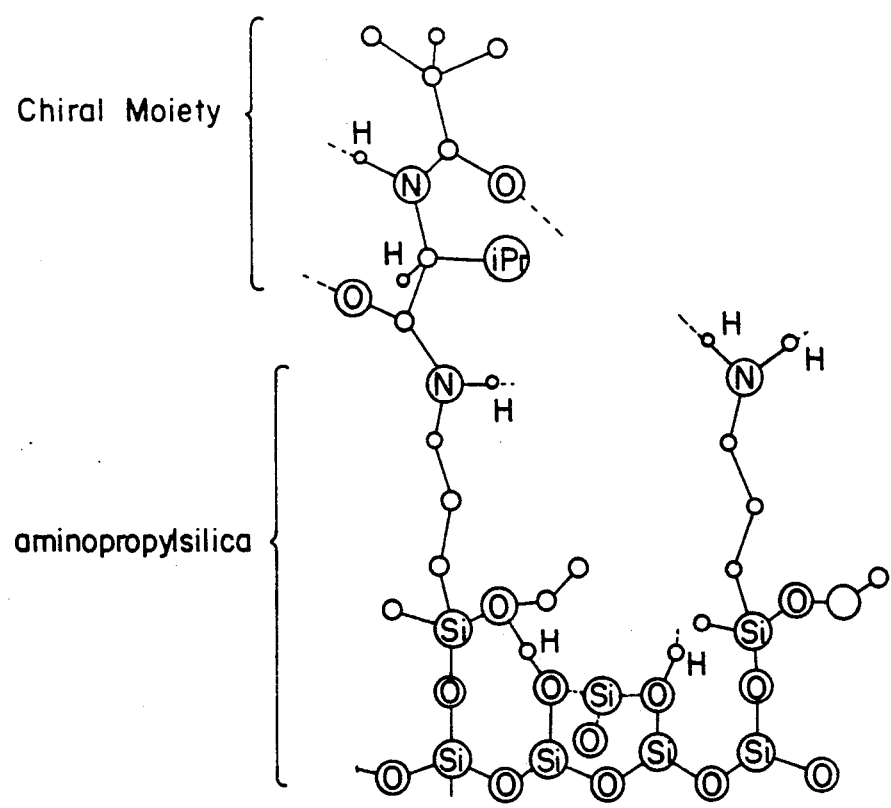
FIG. 3 is a schematic diagram showing the molecular structure of the prior art stationary phase.
Figure 4:
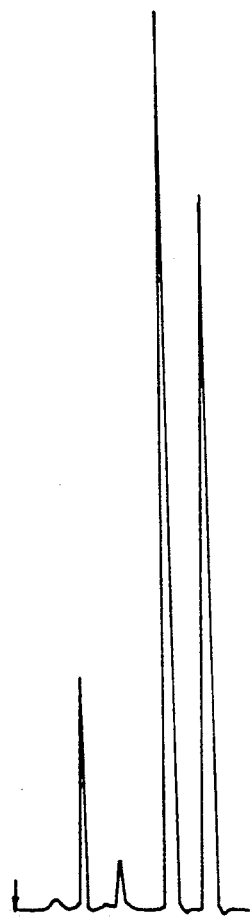
FIG. 4 is a chromatogram obtained with the stationary phase of the invention.
Figure 5:
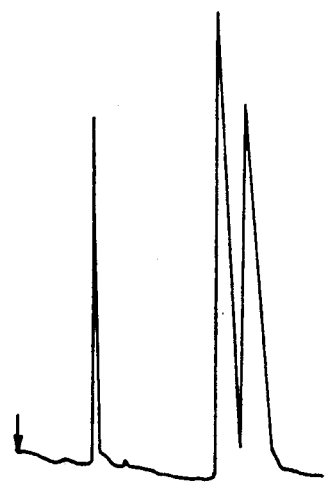
FIG. 5 is a chromatogram obtained with the corresponding stationary phase without sub-anchors and spacers. The horizontal axis stands for retention time and the vertical axis stands for quantity.

The following mechanisms may be postulated for the improved resolution power of the stationary phase of the invention over the conventional stationary phases. In the conventional stationary phases for chromatography, a chiral moiety is directly coupled chemically to an aminoalkylsilica. As shown in FIG. 2 by way of example, the molecule-to-molecule interaction between the N-acylamino acid amide type chiral moiety and the amino acid derivative, as the object of optical resolution, results from steric hindrance between the functional groups attached to the two asymmetric carbon atoms and thus optical resolution takes place accordingly. Because of the direct coupling of the chiral moiety and the aminopropylsilica (aminoalkylsilica) in the conventional stationary phase, there is not sufficient space available for such interaction between the molecule as the object of optical resolution and the chiral moiety as shown in FIG. 3.

Figure 1:
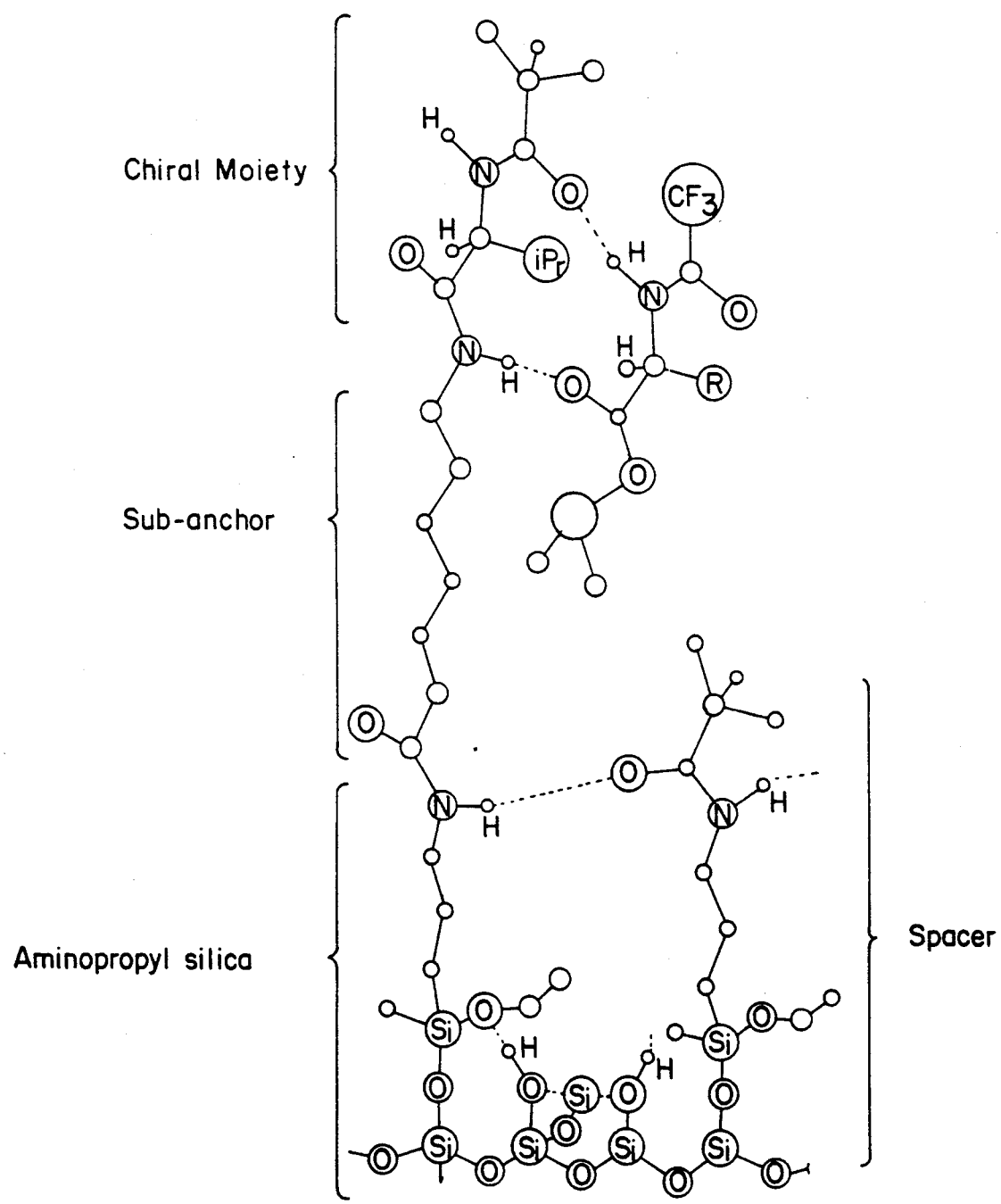
FIG. 1 is a schematic diagram showing the manner of fractionation with the stationary phase of the invention.

In contrast, the stationary phase of the present invention has a sub-anchor moiety between the aminopropylsilica (anchor moiety) and the chiral moiety as shown in FIG. 1 to provide an increased distance therebetween. Moreover, when an aminoalkyl group is protected with a protective group (spacer) such as a pivaloyl group and is provided among the chirality-recognizing groups on the surface of the carrier, there is obtained enough space among adjacent groups for chiral-recognition. When the unreacted aminopropyl(alkyl) group is protected with an appropriate protective group such as pivaloyl, the undesirable interaction between the hydrogen bond and the molecule as the object of optical resolution is precluded.

The method for producing the stationary phase of the invention is now described in detail. In the stationary phase of the invention, the sub-anchor may be introduced by $NH_2—(CH_2)n—COOH$. The chiral moiety is generically represented as $A—CO—$ for convenience's sake. Prior to joining the chiral moiety to the sub-anchor, the C-terminal of the $NH_2—(CH_2)n—COOH$ is first protected in the form of methyl ester as follows.

$$NH_2—(CH_2)_n—COOH + CH_3OH \xrightarrow[\text{reflux}]{HCl}$$ [I]

$$NH_2—(CH_2)_n—COOCH_3 + H_2O$$

On the other hand, the free acid portion of the chiral moiety is converted to an active ester by the following reaction.

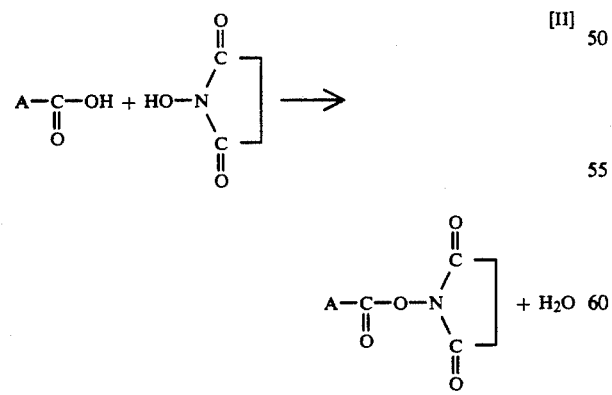

Then, the sub-anchor of formula [I] is reacted with the chiral moiety of formula [II] in the following manner to provide a chiral moity with sub-anchor of formula [III].

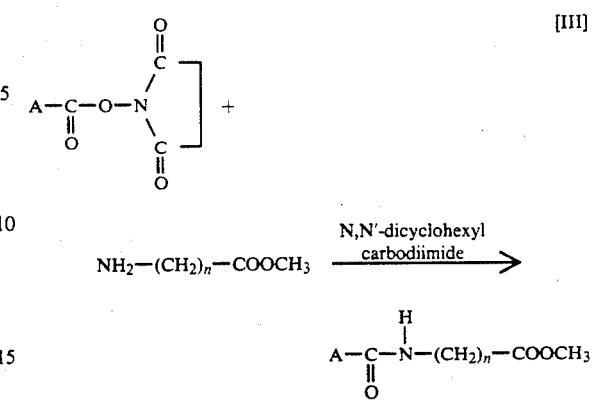

This chiral moiety with sub-anchor of formula [III] is then treated as follows.

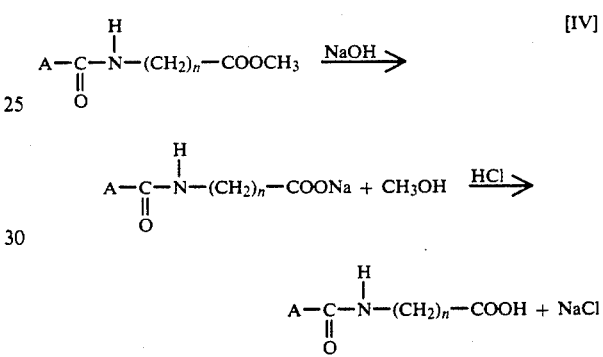

The resulting compound of formula [IV] is bound to an aminoalkylsilica (for example, aminopropylsilica) as follows.

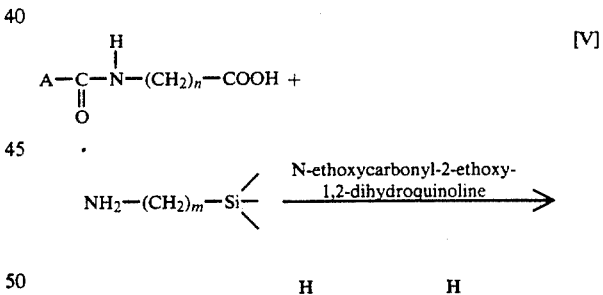

A reagent such as pivalic acid is added at the final stage of production of said compound [V] to react the reagent with the free amino groups not joined to a chiral moiety having sub-anchor, on the silica support. Then, the reagent ensures the space among adjacent groups for chiralrecognition and the free amino groups are protected.

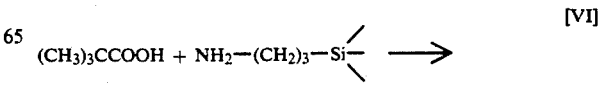

-continued

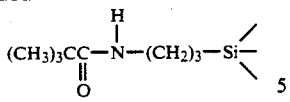

Preparation of a Column

The stationary phase obtained as above is washed thoroughly with a solvent such as tetrahydrofuran (THF), methanol, etc. and removing the solvent remained. By the slurry method, the stationary phase prepared is packed into an analytical column for HPLC. Thus, the stationary phase material of the present invention is packed into a chromatographic column and used as a stationary phase for liquid chromatography.

The chromatographic stationary phase of the present invention has a high chiral-recognition ability and, permits efficient resolution of optical isomers.

The following examples are further illustrative of the present invention.

EXAMPLE 1

N-Pivaloyl-L-valine and 6-aminohexanoic acid ($H_2N(CH_2)_5COOH$) were used as A—CO—OH and the sub-anchor, respectively.

$^1$H NMR for the chiral moiety ($CDCl_3$ 300 MHz): δ0.97(6H), δ1.23(9H), δ2.25(1H), δ4.60(1H), δ6.30(1H), δ10.80(1H).

(1) Synthesis of 6-aminohexanoic acid methyl ester hydrochloride

To 500 ml of ice-cooled methanol was added 130 ml of thionyl chloride in small portions with constant stirring. Then, at room temperature, 66 g (0.5 mol) of 6-aminohexanoic acid was added and the mixture was stirred for 24 hours.

After completion of the reaction, the solvent was removed and for removal of residual $H_2O$ and HCl, the addition of methanol and subsequent concentration were repeated a few times to give 83.6 g (0.46 mol) of methyl 6-aminohexanoate hydrochloride.

(2) Synthesis of methyl N-pivaloyl-L-valine-6-aminohexanoate

In 1 l of ethyl acetate was dissolved 30 g (0.15 mol) of N-pivaloyl-L-valine and the solution was cooled to −20° C. Then, 37.1 g (0.18 mol) of N,N'-dicyclohexylcarbodiimide and 20.7 g (0.18 mol) of N-hydroxysuccinimide were added and the reaction was conducted overnight. The reaction mixture was then allowed to return to room temperature and the by-product dicyclohexylurea was filtered off. The filtrate was cooled again to −20° C. and 32.7 g (0.18 mol) of methyl 6-aminohexanoate hydrochloride and 40 ml (0.36 mol) of N-methylmorpholine were added. The mixture was stirred with cooling for 48 hours.

The solution was then allowed to return to room temperature and the insoluble matter was filtered off. The ethyl acetate solution was washed successively with $H_2O$/2% HCl/$H_2O$/5% $NaHCO_3$/$H_2O$ to remove the amine and acid components from the solution. The solution was then dehydrated over anhydrous $MgSO_4$ and the solvent was distilled off under reduced pressure to give 44 g (0.134 mol) of methyl N-pivaloyl-L-valine-6-amino-hexanoate.

$^1$H NMR ($CDCl_3$ 300 MHz): δ0.97(6H), δ1.23(9H), δ1.3, δ1.5, δ1.6(6H), δ2.25(1H), δ2.4(2H), δ3.2, δ3.3(2H), δ3.7(3H), δ4.60(1H, δ6.30(1H), δ10.80(1H).

(3) N-Pivaloyl-L-valine-6-amino-hexanoic acid

In 500 ml of methanol was dissolved 44 g of methyl N-pivaloyl-L-valine-6-aminohexanoate followed by addition of 150 ml of 1N sodium hydroxide and the mixture was stirred at room temperature for 45 minutes. The ethanol was then evaporated off and 1N HCl and, then, ether were added to the residue. The mixture was shaken to extract the reaction product into the ether. The water layer was removed and the ether layer was dried over magnesium sulfate anhydride and concentrated to dryness under reduced pressure to give 35 g (0.112 mol) of the desired compound.

(4) Coupling to aminopropyl-silica 2.5 g of Aminopropylsilica was added into 3.91 g (0.0125 mol) of N-pivaloyl-L-valine-6-aminohexanoic acid and 1.28 g (0.0125 mol) of pivalic acid disolved in 150 ml of tetrahydrofuran. The mixture was stirred at room temperature for 1 hour. Then, 6.15 g (0.025 mol) of 1-ethoxycarbonyl-2-ethoxy-1,2-dihydro-quinoline (EEDQ) was added and the mixture was further stirred for 48 hours. After completion of the reaction, the silica was recovered by filtration through a 1.0 μm Teflon filter and suspended in methanol, acetone and ether in the order mentioned to remove impurities. The silica was then thoroughly dried and packed into a column in the usual manner.

Coupling rate (%) to aminopiopyl-silica by elemental analysis for C and N: pivaloyl (spacer), 58%; N-pivaloyl-L-valine (sub-anchor), 42%.

The above stationary phase material was packed into an HPLC column (4 mm in. dia. ×25 cm long) by the conventional slurry-packing method to provide a liquid chromatographic column. Using this column, a sample was fractionated under the following conditions to evaluate the fractionating power of the column.

Mobile phase: n-Hexane/dichloromethane (99.5/0.5) 1 ml/min
Detector: UV detector (254 nm)
Sample: N-TFA-phenylalanine isopropyl ester FIG. 1 shows the chromatogram obtained with the stationary phase of the invention of FIG. 2 is the chromatogram obtained with the prior art stationary phase having the same chiral moiety but no sub-anchor moiety. The horizontal axis stands for retention time and the vertical axis stands for quantity. The use of the stationary phase of the invention resulted in a markedly improved resolution of D- and L-isomers. While the peak obtainable by the prior art shows a fair amount of tailing even when alcohol is added to the mobile phase (n-hexane/isopropyl alcohols=99.8/0.2), the present invention promises sharp peaks with good symmetry even in the absence of alcohol, indicating that the interaction takes place efficiently and sufficiently in the present invention.

Resolution coefficient (α): the mobile phase (n-hexane/isopropanol =95:5)

| Sample | Example 1 | prior art (without sub-anchor and spacer) |
|---|---|---|
| α-alanine | 1.55 | 1.18 |
| α-valine | 1.85 | 1.29 |

| Sample | Example 1 | prior art (without sub-anchor and spacer) |
|---|---|---|
| α-leucine | 2.24 | 1.44 |

Each sample was converted into N-3,5-dinitrobenzoyl, isopropyl ester derivative for analysis.

EXAMPLE 2

A stationary phase was prepared according to the same manner as described in Example 1 except that the chiral moiety and sub-anchor were changed for N-(tert-butylamino-carbonyl) -L-valine and 9-amino nonanoic acid, respectively. The resulting stationary phase for liquid chromatography has a high chirality-recognizing ability as follows.

$^1$H NMR for chiral moiety (CDCl$_3$ 300 MHz): δ0.95(6H), δ1.25(9H), δ2.28(1H), δ4.75(1H), δ9.60(1H), δ10.10(1H), δ11.00(1H).

$^1$H NMR (CDCl$_3$ 300 MHz) for methyl N-(tert-butylamino-carbonyl) -L-valine-9-amino nonanate: δ0.95(6H), δ1.25(9H), δ1.3, δ1.5, δ1.6(6H), δ2.28(1H), δ2.4(2H), δ3.2, δ3.3(2H), δ3.7(3H), δ4.75(1H), δ9.60(1H), δ10.10(1H), δ11.00(1H).

Coupling rate (%) to aminopropyl-silica by elemental analysis for C and N: Pivaloyl (spacer), 62%; N-carbamoyl-L-valine (sub-anchor) 38%.

Resolution coefficient (α):

| Sample | Example 2 | prior art (without sub-anchor and spacer) |
|---|---|---|
| α-alanine | 1.42 | 1.12 |
| α-valine | 1.67 | 1.34 |
| α-leucine | 2.98 | 1.42 |

Each sample was converted into N-acetyl, methyl ester derivotive for analysis.

What is claimed is:

1. A stationary phase for enantiomeric resolution liquid chromatography, comprising: a support sized and dimensioned for chromatographic separation having a chiral group of the formula:

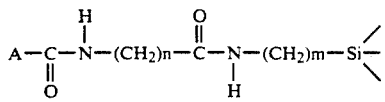

wherein A—CO— represents a chiral moiety; m represents an integer of not less than 3; and n represents an integer of not less than 5.

2. The stationary phase of claim 1, wherein a protective group is joined to any free aminoalkyl silica group bound to said support.

3. The stationary phase of claim 2, wherein said protective group is a pivaloyl group.

4. The stationary phase of claim 2, wherein said chiral moiety is an N-acyl amino acid, an N-carbamoyl amino acid, or N-carbamoyl-α-aromatic alkylamine.

5. The stationary phase of claim 1 or 2, wherein m means an interger of 3 to 6.

6. The stationary phase of claim 1 or 2, wherein said support is silica gel.

7. The stationary phase of claim 1, wherein —HN—(CH$_2$)n—CO— moiety is derived from at least one aminoalkylsilane selected from the group consisting of 6-aminohexyl-alkoxysilane, 6-aminohexyl-halogenosilane, 3-aminopropyl-alkoxysilane, 3-aminopropyl trihalogenosilane.

8. The stationary phase of claim 1 or 2, wherein n represents an integer of 5 to 10.

9. The stationary phase of claim 1, wherein said chiral moiety is at least one residue of amino acid selected from the group consisting of an N-acyl amino acid, an N-carbamoyl amino acid and a N-carbamoyl-α-aromatic alkyl amine.

10. The stationary phase of claim 9, wherein N-acyl amino acid is N-pivaloyl-L-valine or N-3,5-dinitrobenzoyl -D-phenylglycine.

11. The stationary phase of claim 9, wherein N-carbamoyl amino acid is N-carbamoyl-leucine or N-carbamoyl-valine.

12. The stationary phase of claim 9, wherein N-carbamoyl-α-aromatic alkyl amine is N-carbamoyl-α-(1-naphthyl) ethyl amine.

* * * * *